United States Patent
Olivo et al.

(10) Patent No.: US 11,497,643 B2
(45) Date of Patent: Nov. 15, 2022

(54) SYSTEM FOR SUPPORTING A LINER ON A FRAME ELEMENT

(71) Applicant: OSSUR ICELAND EHF, Reykjavik (IS)

(72) Inventors: Jared Olivo, Foothill Ranch, CA (US); Lindsay Frost, Foothill Ranch, CA (US); Patrick Kiruki, Foothill Ranch, CA (US)

(73) Assignee: OSSUR ICELAND EHF, Reykjavik (IS)

(*) Notice: Subject to any disclaimer, the term of this patent is extended or adjusted under 35 U.S.C. 154(b) by 375 days.

(21) Appl. No.: 16/037,100

(22) Filed: Jul. 17, 2018

(65) Prior Publication Data

US 2019/0021893 A1   Jan. 24, 2019

Related U.S. Application Data

(60) Provisional application No. 62/534,966, filed on Jul. 20, 2017.

(51) Int. Cl.
*A61F 5/01* (2006.01)
*A61F 2/78* (2006.01)
*A61F 2/80* (2006.01)

(52) U.S. Cl.
CPC .............. *A61F 5/0111* (2013.01); *A61F 2/78* (2013.01); *A61F 2/7812* (2013.01); *A61F 2/80* (2013.01);

(Continued)

(58) Field of Classification Search
CPC .. A61F 5/0111; A61F 5/01; A61F 2005/0181; A61F 13/062; A61F 5/013;

(Continued)

(56) References Cited

U.S. PATENT DOCUMENTS 4,803,975 A * 2/1989 Meyers ................. A61F 5/0123
2/22
6,066,110 A * 5/2000 Nauert .................. A61F 5/0123
602/16

(Continued)

FOREIGN PATENT DOCUMENTS

WO    2005007022 A2    1/2005

OTHER PUBLICATIONS

ScienceDirect—Shrinkage Stress overview and definition (Year: 2021).*

(Continued)

*Primary Examiner* — Alireza Nia
*Assistant Examiner* — Trisha Talapatra
(74) *Attorney, Agent, or Firm* — Workman Nydegger

(57) ABSTRACT

A system for supporting a liner on a frame element includes a liner and a frame element. A fastener connects the liner to the frame element, such that the fastener corresponds to an aperture defined by the frame element. The fastener is configured and dimensioned to removably secure to the frame element at the at least one aperture. The frame element comprises a semi-rigid or rigid base frame element, and an interface layer secured about the base frame element. The interface layer is formed from a resilient material more compressible than the base frame element, and the liner is more flexible than the interface layer.

8 Claims, 6 Drawing Sheets

(52) U.S. Cl.
CPC .......... *A61F 5/0123* (2013.01); *A61F 5/0125* (2013.01); *A61F 2002/7831* (2013.01); *A61F 2002/7875* (2013.01); *A61F 2005/0137* (2013.01); *A61F 2005/0172* (2013.01)

(58) Field of Classification Search
CPC ............ A61F 2005/0195; A61F 5/0125; A61F 2005/0132; A61F 2005/0137; A61F 5/0193; A61F 5/0195; A61F 5/0169; A61F 5/0172; A61F 5/0174; A61F 5/0176; A61F 5/0102–0118; A61F 5/0123–0127; A61F 2005/0172–0176; Y10T 428/24322; Y10T 428/24723; A44B 17/0029; A44B 17/0023
USPC .............................................. 623/36; 602/27
See application file for complete search history.

(56) References Cited

U.S. PATENT DOCUMENTS

| | | | |
|---|---|---|---|
| 7,479,122 | B2 | 1/2009 | Ceriani et al. |
| 7,727,174 | B2 | 6/2010 | Chang et al. |
| 7,941,867 | B2 | 5/2011 | Olson |
| 8,043,244 | B2 | 10/2011 | Einarsson et al. |
| 8,048,013 | B2 | 11/2011 | Ingimundarson et al. |
| 8,282,588 | B2 | 10/2012 | Ingimundarson et al. |
| 8,292,838 | B2 | 10/2012 | Ingimundarson et al. |
| 8,343,083 | B1* | 1/2013 | Fencel .................. A61F 5/0123 602/23 |
| 8,506,866 | B2 | 8/2013 | Deseure et al. |
| 8,512,267 | B2 | 8/2013 | McCune et al. |
| 8,679,044 | B2 | 3/2014 | Thorgilsdottir et al. |
| 8,740,829 | B2 | 6/2014 | Lee et al. |
| 8,951,217 | B2* | 2/2015 | Joseph ................ A61F 5/05841 602/7 |
| 9,323,221 | B2 | 4/2016 | Villar et al. |
| 9,370,911 | B2 | 6/2016 | Maurice |
| 9,375,341 | B2 | 6/2016 | Ingimundarson et al. |
| 9,399,337 | B2 | 7/2016 | Curnutt |
| 9,474,334 | B2 | 10/2016 | Jonsson et al. |
| 9,498,025 | B2 | 11/2016 | Omarsson et al. |
| 9,668,907 | B2 | 6/2017 | Romo et al. |
| 2004/0019306 | A1* | 1/2004 | Brewer .................... A61F 5/013 602/21 |
| 2007/0276510 | A1 | 11/2007 | Becker et al. |
| 2010/0331750 | A1* | 12/2010 | Ingimundarson ..... A61F 5/0123 602/26 |
| 2012/0177927 | A1 | 7/2012 | Cheng |
| 2013/0204172 | A1* | 8/2013 | Viehweg ............... A61F 5/0102 602/26 |
| 2014/0213953 | A1* | 7/2014 | Heyd .................... A61F 5/0111 602/27 |
| 2014/0261229 | A1 | 9/2014 | Bao et al. |
| 2014/0298624 | A1* | 10/2014 | Omarsson .............. A44B 11/02 24/265 EC |
| 2014/0323937 | A1* | 10/2014 | Knecht ................. A61F 5/0123 602/16 |
| 2016/0008157 | A1 | 1/2016 | Brookover et al. |
| 2016/0051389 | A1* | 2/2016 | Seligman .............. A61F 5/0123 602/16 |
| 2016/0081838 | A1 | 3/2016 | Ledezma et al. |
| 2016/0206448 | A1 | 7/2016 | Klutts |
| 2016/0250782 | A1 | 9/2016 | Krass et al. |
| 2016/0271901 | A1 | 9/2016 | Demange |
| 2016/0297183 | A1 | 10/2016 | Demange et al. |
| 2016/0324666 | A1* | 11/2016 | Barberio ............... A61F 5/0118 |
| 2017/0151072 | A1 | 6/2017 | Mahon et al. |
| 2017/0189241 | A1* | 7/2017 | Joseph ................. A61F 13/046 |

OTHER PUBLICATIONS

TheFreeDictionary.com—definition of "recess", p. 1 (Year: 2021).*
International Search Report from PCT Application No. PCT/US2018/042374, dated Nov. 23, 2018.

* cited by examiner

SYSTEM FOR SUPPORTING A LINER ON A FRAME ELEMENT

FIELD OF THE DISCLOSURE

The disclosure relates to a system for providing a frame element with a liner, particularly for a rigid frame element in an orthopedic or prosthetic device.

BACKGROUND

Removable liners are commonly used for frame elements in orthopedic devices as a way to provide added comfort and/or protection while also affording the advantages of removability. A removable liner may be removed for replacement, repair, or cleaning without incurring any inconvenience or changes to the frame element to which the removable liner is attached.

Common attachment means for a liner include hook and loop fastener elements, but hook and loop fastener elements have significant drawbacks. Attachment may be imprecise, the connection between hook and loop may not be strong enough to withstand forces such as shear forces which may cause unintended separation of articles, and hook and loop fastener materials may not be sufficiently durable for articles intended for long-term and/or heavy duty use. Hook and loop fastener elements may prove frustrating and difficult to use repeatedly, especially for an elderly person, a person having poor dexterity, or a person recovering from an injury.

In order to properly mount a liner on a frame element using hook and loop fastener, a user may make multiple attempts to attain to the correct alignment, because hook and loop fastener inherently provides a range of attachment configurations (the only requirement being that a portion of the hook portion and a portion of the loop portion are in contact). This can make attaching a liner to a frame element time-consuming and cumbersome.

Hook and loop fastener may not provide a desired attachment strength, and may prove insufficient to withstand forces that result in unintentional detachment of the liner. Increasing the strength of attachment via hook and loop fastener may require larger surface areas of hook material, adding to the difficulties of proper alignment and ease of use.

Frame elements in orthopedic devices may need to be rigid to support a user's weight, but rigid materials suitable for use as a frame element, such as metallic materials, may cause discomfort for a user (such as by having hard edges that cause chafing or pressure points), may lack aesthetic appeal, and may not be capable of properly supporting or protecting frame attachments from dust, dirt, impact, wear and tear, and other factors. All of these factors can impede long-term use of the frame element.

There is need for an improved liner for a corresponding frame element that is precisely mountable, strong, durable, and easy to use, and has an interface layer for frame elements that address the aforementioned problems.

SUMMARY

Shortcomings of known liners for frame elements are solved by providing a system for supporting a liner on a frame element. The system may comprise a liner, such as a compressive pad for increasing user comfort, a frame element, and at least one fastener connected to the liner and the at least one aperture corresponding to the at least one fastener and defined by the frame element. The at least one fastener may be configured and dimensioned to releasably secure at the at least one aperture. The frame element may be semi-rigid or rigid, and the liner serves as a buffer between the frame element and the user, possessing softer or compressive properties that the frame element lacks to improve comfort and wearability, and prevent migration.

According to a variation of the system, an interface layer may be molded and secured onto the frame element. The interface layer may define apertures or other fastener features for securing the liner thereto, or alternatively may dually serve as an interface and as a liner. The interface layer may possess compressive properties that can replace or augment a liner. The liner may secure directly to the frame element, and it may not be necessary to provide the interface layer.

The system advantageously provides a more accurate mounting mechanism for a liner for a frame element, in that whereas hook and loop fasteners allow for a certain range of possible attachment configurations, throughout which range at least a portion of the hook and loop materials are joined, some arrangements of which may cause poor fit and discomfort, the system according to the disclosure provides only one possible (and correct) attachment configuration, ensuring that the liner is attached in a precise and intended arrangement.

The system also provides a stronger attachment between liner and frame element that better withstands forces such as a shear forces that could otherwise result in unintentional detachment of the liner from the frame element if connected by hook and loop fastener, while not being so strong that an unaided user could not remove the liner with relative ease. The system of the disclosure enables the liner to be suitable for a variety of potentially high-impact or heavy-duty uses where hook and loop fastener would be insufficient or ineffective, such as athletic activities. The liner is also an improvement in reliability for normal, everyday uses.

The system provides a more durable attachment between liner and frame element. Whereas hook and loop fastener may wear out over time or lose effectiveness, the at least one fastener and corresponding at least one aperture may be configured to provide robust and therefore more reliable attachment over many uses, owing to the properties and configuration of the liner, the at least one fastener, and the interface layer defining the at least one aperture.

The system also provides an easier-to-use mechanism for persons who must attach or detach the liner; users may find it more simple and easy to press in and pull out the at least one fastener from the at least one aperture, especially if guided by a snap feature, than to configure multiple arrays of hook and loop fastener material into a precise configuration. A user may make multiple attempts to properly mount a liner which attaches through hook and loop fastener, owing to the imprecise nature of hook and loop fasteners discussed above. Such a user will benefit from a liner attachment mechanism that requires only one simple attachment attempt.

The system also provides a more comfortable and durable frame element by providing the interface layer according to the system of the disclosure. By providing the interface layer that extends over at least a portion of a rigid base frame element, and providing additional cushioning material and coverage of various frame element features and attachments, numerous problems such as discomfort to a user and damage to a frame element or frame attachments are overcome.

In a representative embodiment of the system according to the disclosure, a liner is arranged to correspond to a frame element in a knee orthosis. The liner comprises fasteners that are non-removably secured to the liner and comprise a domed head portion with a narrow shaft portion configured to removably secure to corresponding apertures in the interface layer of the corresponding frame element. The fasteners and apertures are configured to provide a "snap" sound or sensation when the fasteners are properly inserted into the apertures, confirming to a user that the connection has been properly made. Of course, the fasteners may be reversed so that the liner possesses apertures and the frame element bears the fasteners.

In this representative embodiment, the liner and the interface layer further comprise extended portions and recessed portions to better cushion, support, and provide breathability to a user and to accommodate and complement frame attachments such as straps. Extended portions and recessed portions also advantageously allow the liner and frame element to be flexible and adaptable to different configurations which may be required in order to better fit an individual wearer's dimensions.

Additional features and advantages of the disclosure will be set forth in the description that follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

Figure 1:
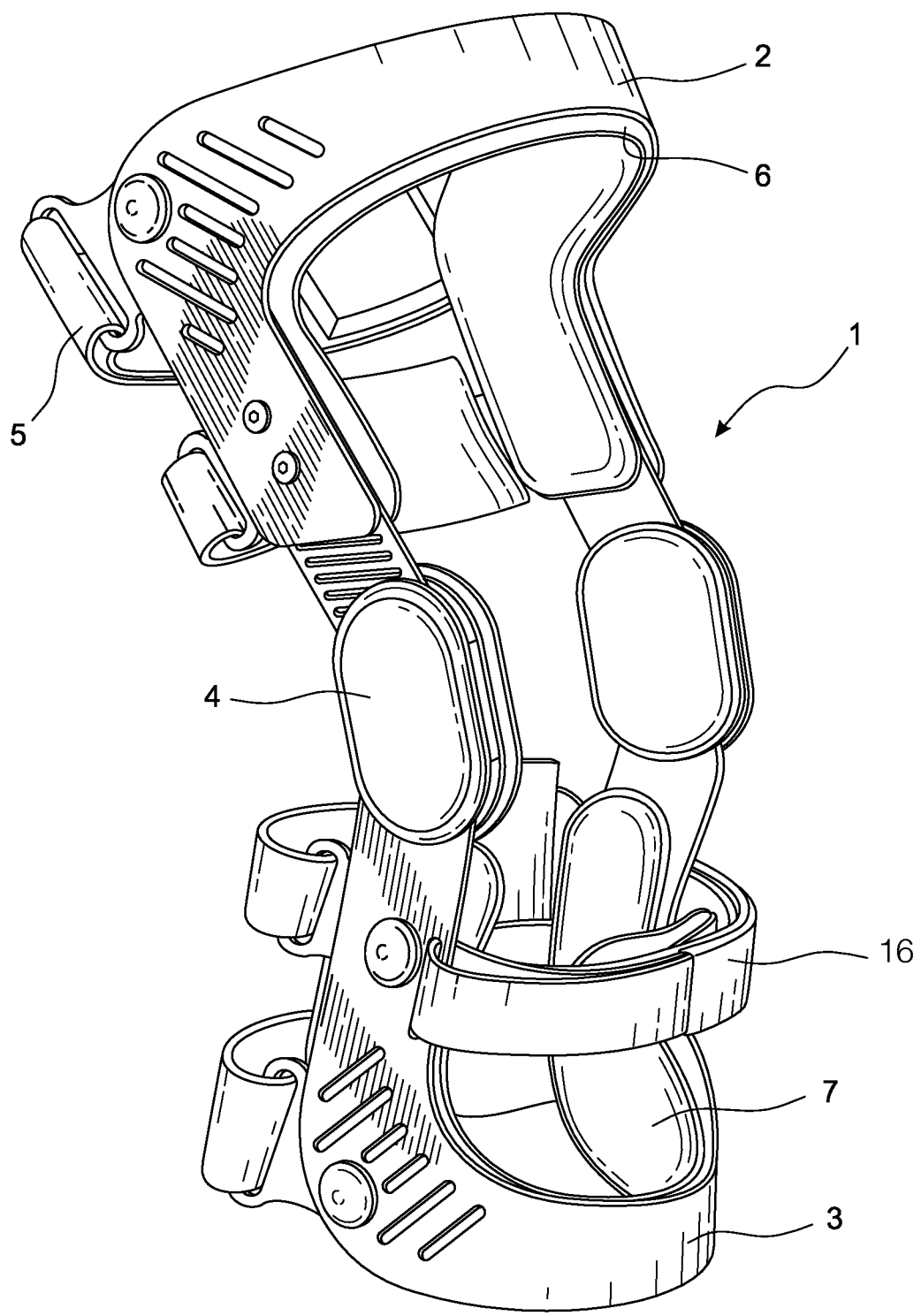
FIG. 1 is a profile view of a prior art knee brace comprising an upper or proximal cuff, a lower or distal cuff, and a hinge and hinge members.

The drawing figures are not necessarily drawn to scale, but instead are drawn to provide a better understanding of the components, and are not intended to be limiting in scope, but to provide exemplary illustrations. The figures illustrate exemplary configurations of a liner for a corresponding frame element, and in no way limit the configurations of a liner for a corresponding frame element and components according to the present disclosure.

DETAILED DESCRIPTION OF VARIOUS EMBODIMENTS

For further ease of understanding the representative embodiments of a liner for a corresponding frame element, these terms may be used with the features of the exemplary embodiments.

The term "fastener" has its ordinary meaning and refers to a device, material, or implement that functions to secure materials or components in place. The term "liner" has its ordinary meaning and refers to an article configured to line and/or extend at least partially over, around, or on another article. The term "frame element" has its ordinary meaning and refers to a component of a frame or structure.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however such support members or shells may have some degree of flexibility or resiliency.

The term "overmold" has its ordinary meaning and refers to material that is added over an existing article or material. Overmolding is generally understood as a process where a single part is created using two or more different materials in combination. A substrate, such as the frame element, is partially or fully covered by a subsequent material, as in the interface layer. The frame element can be constructed from a variety of materials, and in an exemplary embodiment is formed from a metal, such as aluminum or titanium. The interface layer may be a plastic, such as a thermoplastic elastomer (TPE). The interface layer is chemically or mechanically bonded to interlock with the frame element. The frame element may be definitively formed, and the interface layer is molded to yield to the definitive shape of the frame element, and may have shrinkage stresses about the periphery of the frame element to retain the interface element thereon without requiring fasteners or adhesive.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

Reference characters are provided in the claims for explanatory purposes only and are not intended to limit the scope of the claims or restrict each claim limitation to the element in the drawings identified by the reference character.

In a representative embodiment of a system according to the disclosure, a liner is configured to be supported on a frame element, specifically a lower or distal cuff of a knee orthosis. The liner provides added support and comfort for a user of the knee orthosis, while also advantageously being removable so that the liner may be washed, adjusted, or replaced as necessary, or simply when a user needs or desires to wear the orthosis without the liner. Fasteners are connected to the liner and are configured to allow the liner to removably connect to the frame element at apertures defined therein and in an interface layer overmolded onto the frame element.

The frame element is provided with an interface layer that protects the frame element from dust, dirt, impact, and/or corrosion, adds aesthetic appeal, and complements the soft support of the liner, while also defining apertures corresponding to the apertures in the frame element and the fasteners in the liner.

FIG. 1 shows a prior art knee orthosis 1, for example as discussed in greater detail in U.S. patent application publication 2016/0008157, published on Jan. 14, 2016 and incorporated herein by reference. The knee orthosis 1 has a frame element comprising a first or upper cuff 2, a and second or lower cuff 3, connected to one another by hinge members 4. Such knee orthoses may further comprise or support attachments such as straps 5 and other frame accessories, which may attach to and protrude from an outer side of either or both of the cuffs. Liners 6, 7 may be attached to the first and second cuffs 2, 3, respectively.

Figure 2:
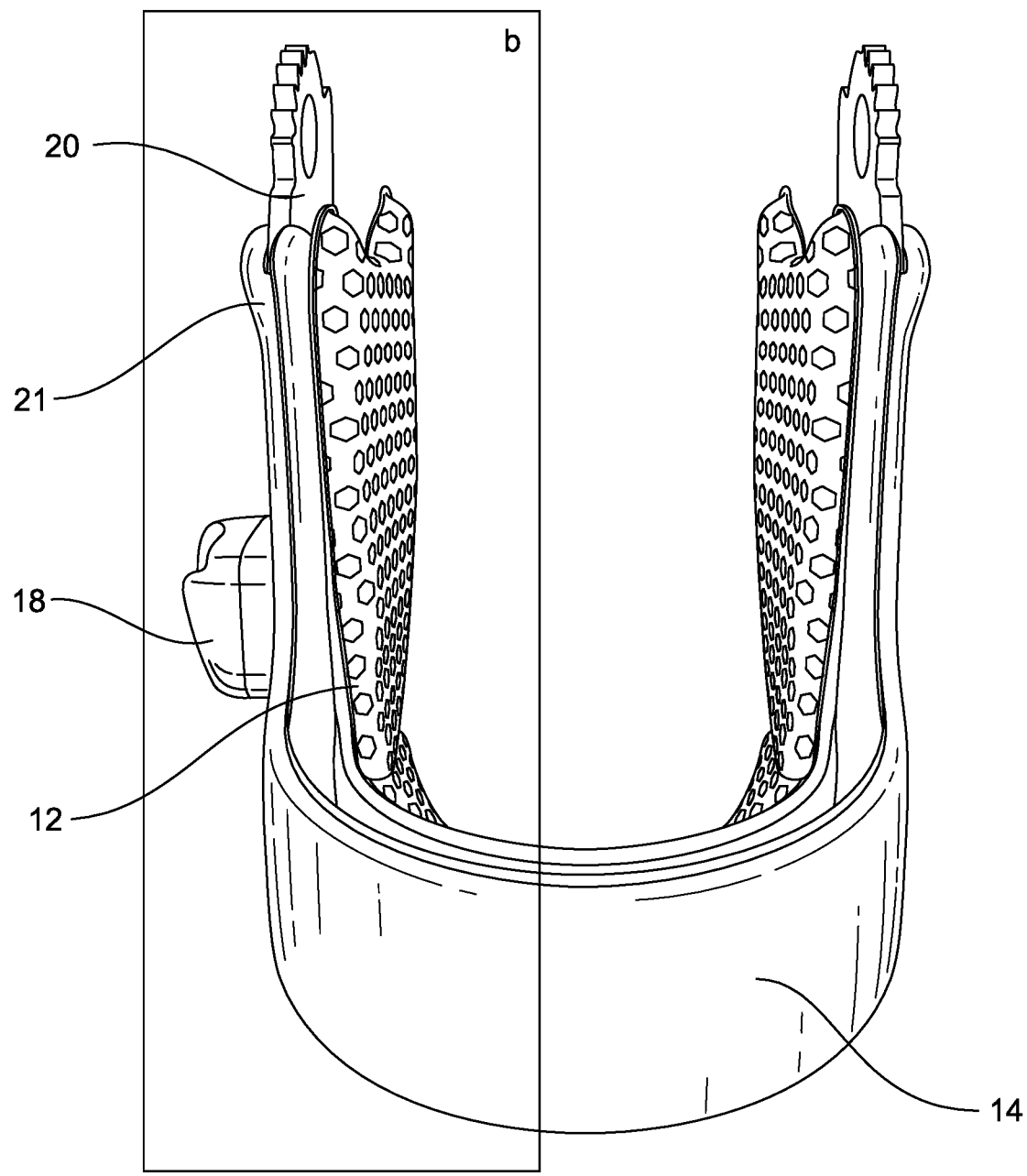
FIG. 2 is a detail plan view of the lower cuff in FIG. 1 further comprising elements of the disclosure.

FIG. 2 presents a detail plan view of the second cuff of the knee orthosis of FIG. 1 in a curved configuration and further comprising, as a representative embodiment, elements of the disclosure. The frame element 14 comprises a semi-rigid or rigid base frame element 20, around at least a portion of which a soft, flexible interface layer 21 extends and secures. The interface layer 21 is substantially compliant and has a smooth surface. The frame accessory 18 attaches to and extends outwardly away from base frame element 20, and the interface layer 21 accommodates the frame accessory 18 by extending around the frame accessory 18.

The frame element 14 is not limited to the combination of the base frame element and the interface layer. The frame element 14 may be provided with only the base frame element, whereupon the liner 12 secures, and is adapted accordingly for the liner to secure. The liner 12 is substantially more flexible than the base frame element, and may be resilient to accommodate a predetermined shape of the base frame element.

The interface layer 21 extends over at least a portion of both an inner or user-facing side and an outer side of the base frame element 20, and defines a connecting portion 23 along a peripheral edge of base frame element 20. The connecting portion 23 may extend slightly beyond the periphery of the base frame element 20 and define an especially compliant region. The connecting portion 23 may define a pinched portion of the interface layer 21 relative to the rest of the interface layer 21.

The liner 12 in this embodiment is coextensive with and attaches to an inner or user-facing side of the overmolded frame element 14 via fasteners and corresponding apertures defined by the interface layer 21 and base frame element 20 (not shown). The liner 12 is configured such that the liner 12 and the overmolded frame element 14 are flush against each other when the liner 12 is attached to the overmolded frame element 14. The interface layer 21 may comprise the same material on both the inner and outer sides of the base frame element 20, or alternatively may comprise different materials at different locations. For example, on an outer side of the base frame element, the interface layer 21 may comprise more or less compressive material than the inner or user-facing side.

In a representative embodiment, the interface layer 21 comprises encapsulated closed-cell foam, as a TPE, bounded by fabric laminate material. The interface layer 21 comprises a layer of polymeric foam of a predetermined density arranged to abut base frame element 20. Coextensive with and attached to the layer of polymeric foam is a discrete layer of elastomer. The interface layer 21 may comprise a TPE, or other plastic that is not foamed. Specifically, the interface layer 21 may consist of a plastic of any type described herein.

Figure 5:
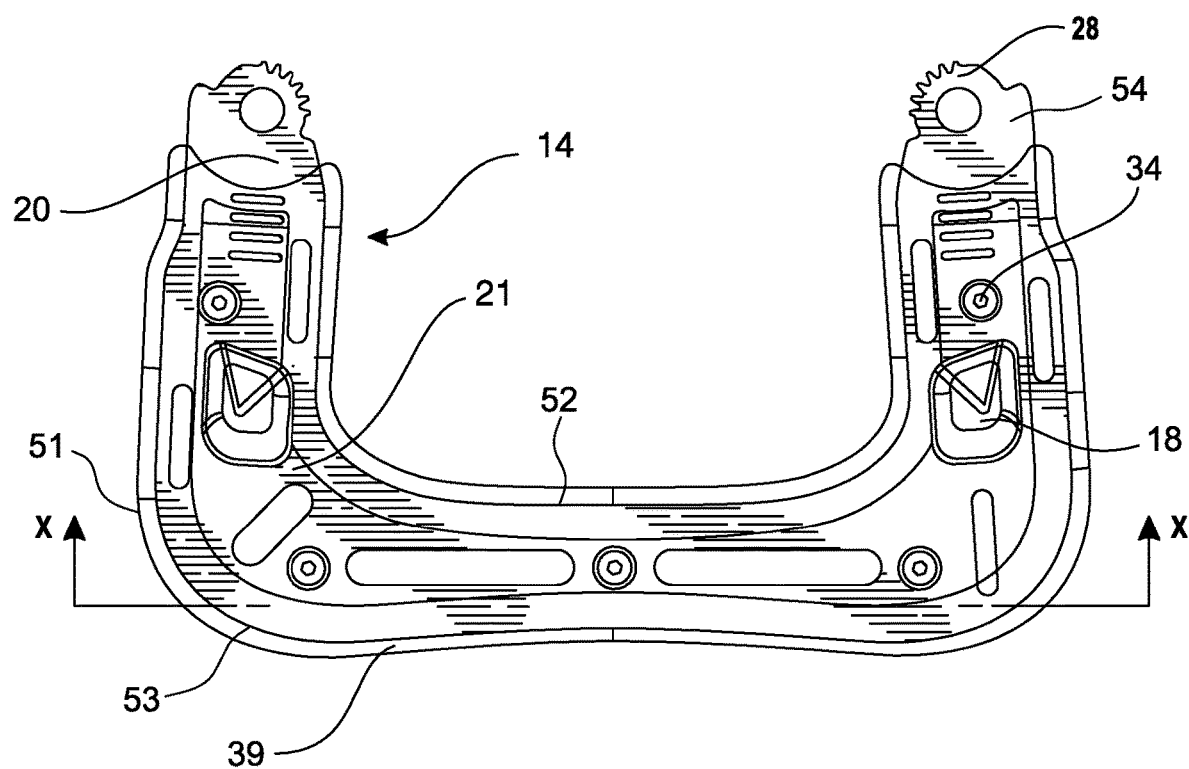
FIG. 5 is a plan view of the base frame element of FIG. 3 partially surrounded by the overmold.
Figure 6:
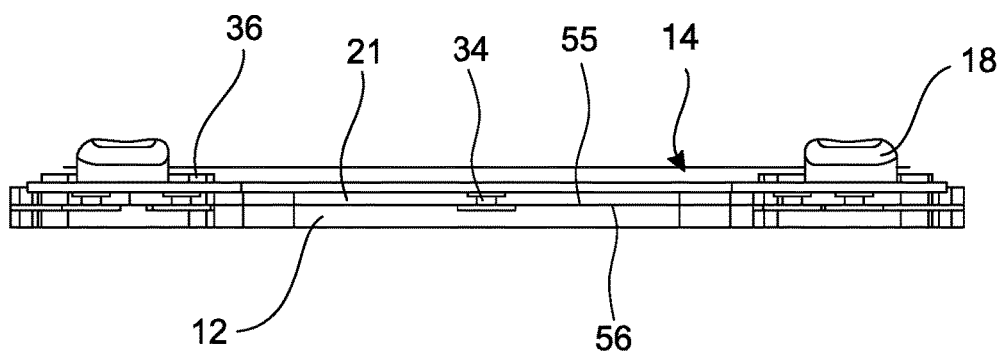
FIG. 6 is an elevational view of the base frame element and the interface layer of FIG. 6 connected to a liner.

As depicted in FIGS. 5 and 6, the interface layer 21 may have a definitive shape that corresponds substantially to or in exactitude to a periphery (such as both inner and outer peripheries or first and second peripheral edges 52, 53, respectively) of the base frame element 20. The interface layer 21 may extend over first and second surfaces 55, 56 of the base frame element 20, thereby encasing at least a segment of the base frame element 20 along a length of the base frame element 20, without substantially departing from or closely approximating the shape of the first and second surfaces 55, 56 of the base frame element.

The interface layer 21 may define a peripheral edge portion 51 extending beyond the inner and outer peripheries 52, 53 of the base frame element 20, to offer protection from the edges of the inner and outer peripheries 52, 53 of the base frame element 20. The peripheral edge portion 51 may define exposed portions 54 devoid of the interface layer 21, such as at the hinge connection of the base frame element 20, or other suitable locations.

The interface layer 21 may be thermoformed at its surface, and advantageously waterproof. This allows the interface layer 21 to be washed, enhancing durability and facilitating long-term use of the frame element 14 by promoting sanitary conditions. Thermoforming also advantageously provides a pleasing smooth aesthetic to the fabric laminate material.

The interface layer 21 is not limited to a combination of foam and fabric laminate material, but rather may comprise a suitable soft and/or compliant material, such as foams (including both open-cell and closed-cell varieties), rubbers, synthetic plastics, textiles, fibers, or any suitable alternative. Compliant material may be bounded by any suitable material, such as fabric or textiles, composite material, plastic film, fiber-reinforced film, or any suitable alternative. Compliant material may be bounded by an active grip material. The interface layer 21 may comprise a single layer of material.

The interface layer 21 may be sufficiently flexible and compliant to adapt to a change in shape of base frame element 20. The base frame element 20 may need to be adjusted to better suit a user's specific dimensions. Owing to the flexible and compliant properties of the core and outer layers of the interface layer 21, the interface layer 21 adapts to the change without detaching from the frame element 20 or reducing coverage thereof.

The interface layer 21 advantageously accommodates the frame accessory 18 and other attachments such as a strap by defining apertures in the interface layer 21 corresponding to apertures defined in the base frame element 20 allowing the frame attachments to attach through the interface layer 21 and directly to the base frame element 20. The interface layer 21 may also advantageously define raised and/or recessed portions that facilitate proper functioning of frame element attachments such as straps, adjustment mechanisms, sleeves, frame members, and etc.

Figure 3:
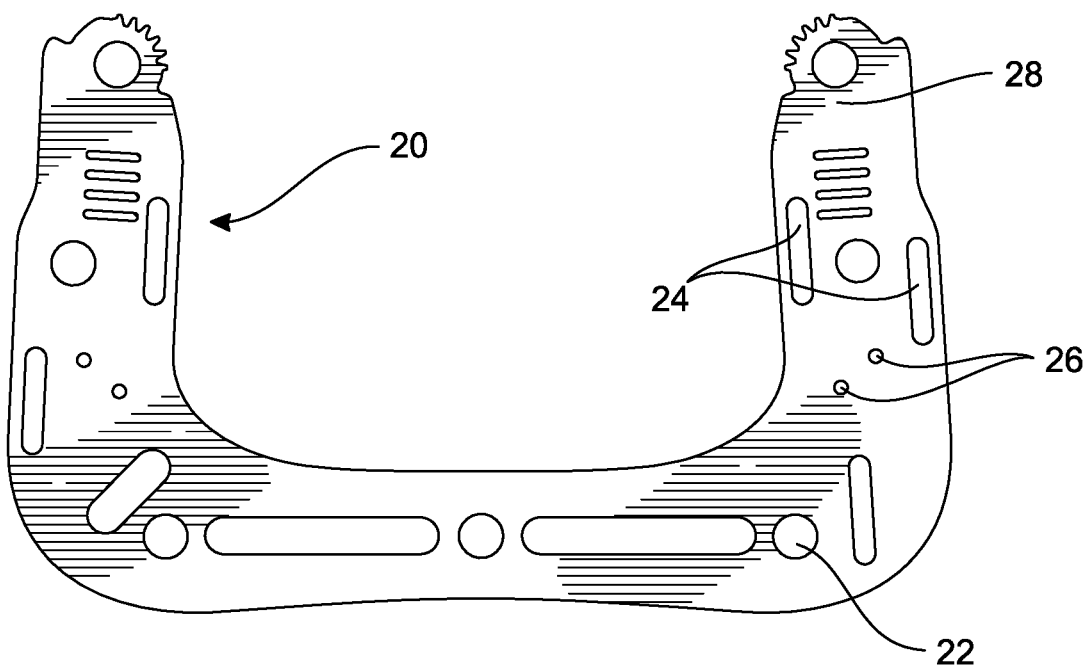
FIG. 3 is a plan view of a base frame element according to the disclosure.

FIG. 3 shows a plan view of the base frame element 20. In the representative embodiment of FIG. 1, the base frame element 20 is a rigid article suitable for bearing a user's weight and comprises a hinge member 28. The base frame element 20 further defines the apertures 22 corresponding to the fasteners of the liner 12. The apertures 24 correspond to frame attachments such as the strap 16, as exemplified in FIG. 1, and allow passage of the strap 16 through the base frame element 20. The apertures 26 correspond to the frame accessory 18 and facilitate direct attachment to the base frame element 20. The apertures 22, 24, 26 may further reduce the weight and cost of the base frame element 20 and/or facilitate greater flexibility and malleability of the base frame element 20.

Figure 4:
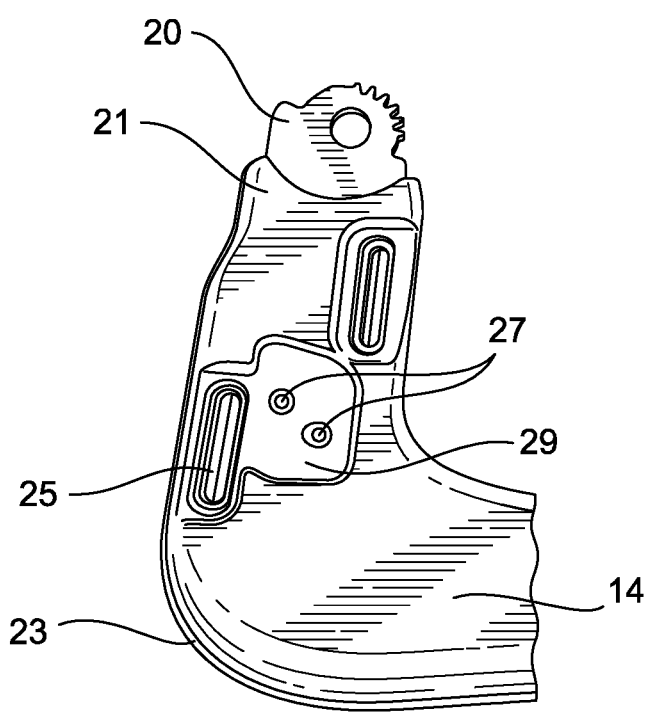
FIG. 4 is a detail plan view of the portion of an overmolded frame element contained in box b of FIG. 2 in a planar configuration.

FIG. 4 depicts a close-up plan view of the portion of the overmolded frame element 14 contained in box b in FIG. 2. The interface layer 21 extends at least partially around the base frame element 20, defining a plurality of apertures corresponding to the apertures 22, 24, 26 in the underlying base frame element 20. The apertures 45 (not shown) in the interface layer 21 correspond to the apertures 22 in the base frame element 20 and facilitate support of the liner 12 on the overmolded frame element 14 by being configured to receive fasteners connected to the liner 12.

The apertures 25 in the interface layer 21 correspond to the apertures 24 defined by the base frame element 20 and allow the overmolded frame element 14 to receive attachments such as the strap 16. The apertures 27 in the interface layer 21 correspond to the apertures 26 in the base frame element 20 and allow the frame accessory 18 to access and connect directly to the base frame element 20.

A recessed portion 29 may surround or abut the apertures 25, 27 to accommodate attachments such as the strap 16 and/or the frame accessory 18 without causing the attachments and/or the interface layer 21 to extend far outwardly from the base frame element 20, thereby reducing bulk, weight, and cost. The recessed portion 29 is defined within a thickness of the interface layer 21, yet is short of extending into the base frame element 20, thereby leaving at least a layer of the interface layer 21 covering the base frame element 20 in the recessed portion 29.

The recessed portions 29 support the strap 16 and the frame accessory 18 by protecting the attachments from any rough surfaces or edges on the base frame element 20, preventing damage from impingement by providing the raised interface layer 21 around the peripheral edges of the attachments, and guiding the strap 16 in an intended direction via raised edges of the interface layer 21.

FIG. 5 depicts a plan view of the overmolded frame element 14 in a planar configuration. The fasteners 34 are shown corresponding to the apertures 22, 45. While the representative embodiment depicts five fasteners, one skilled in the art will understand that fewer than five fasteners (e.g. a single fastener), or more than five fasteners, may suffice for removably attaching the liner 12 to the overmolded frame element 14.

FIG. 6 shows an elevational view of the overmolded frame element 14 taken along line X-X in FIG. 5. The overmolded frame element 14 is shown as being removably attached to the liner 12. Fasteners 34 extend from the liner 12 into the apertures 22 of the interface layer 21 and align with clearances provided by the apertures 45 in the base frame element 20. The fasteners 34 may be configured as dome-shaped fasteners, the dome-shaped head portion configured to permit easy introduction into the apertures 22, 45 but to prevent unintentional removal therefrom.

The fasteners 34 and apertures 22, 45 may be arranged to create a "snap" noise or sensation when a fastener 34 has been successfully introduced in the apertures 22, 45, aiding a user in ascertaining whether attachment has been properly made. Of note, the interface layer 21 may interlock with the base frame element 20 by at least one of the apertures, such that during the overmolding process material from the interface layer extends into the apertures or about the base frame element at the apertures.

When formed in combination with the base frame element 20 and the interface layer 21, the corresponding apertures formed by the base frame element 20 and the interface 21 may be coextensive or extend the base frame element 20 and only a distance into the interface 21. The aperture extends through a first side of the interface layer relative to the base frame element. The aperture may extend through the base frame element, but only into a thickness of the second side of the interface layer relative to the base frame element short of the entire thickness of the interface layer. In this manner, if the aperture extends from a surface on the inner side (adjacent the user's body) of the frame element, the aperture does not extend completely through the frame element to be exposed on an outer side of the frame element, such that the fastener is concealed on the outer side of the frame element because the aperture does not extend fully through the interface layer.

The frame element can be configured so the apertures extend fully through the frame element, both through the interface layer and the base frame element, as in strap slots, or for any other desirable configuration (i.e., the fastener interlocking through the entire thickness of the frame element extending from the inner side of the frame element to lock over the outer side of the frame element.

A base portion 37 of the fasteners 34 may have a wide lip configured to non-removably secure the base portion of fasteners 34 within a body of the liner 12. In an exemplary embodiment, the fasteners 34 are compression molded into liner 12. The base portion 37 and the liner 12 may be configured and comprise material to make the liner 12 sufficiently durable to be mounted on and removed from frame element 30 often without the fastener 34 detaching from the liner 12.

In addition to the recessed portions 29 of the interface layer 21, the interface layer 21 may also feature raised or thickened portions 36. The thickened portions 36 may comprise additional compressible material for greater comfort during handling and/or use of the frame element.

In an embodiment, an inner or user-facing surface of the interface layer 32 is more planar and comprises fewer thickened portions than the outer facing surface of the interface layer 32 so as to better receive, accommodate, and/or be coextensive with the liner 12.

Figure 7:
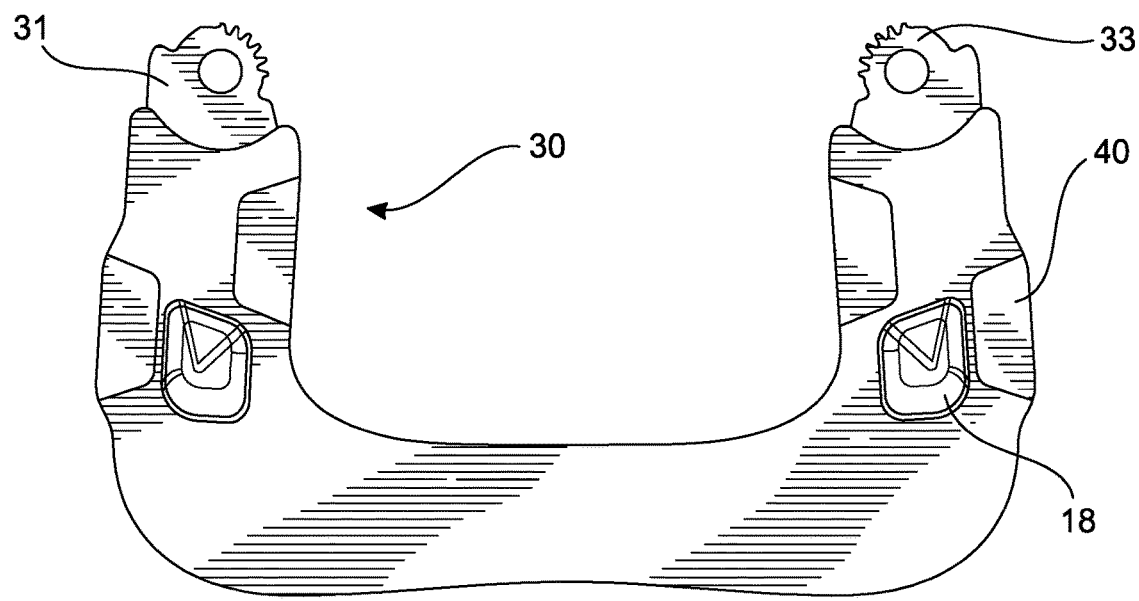
FIG. 7 is a plan view of an alternative embodiment of the base frame element and the interface layer of FIG. 5.

FIG. 7 shows an alternative embodiment of an overmolded frame element 30 for a knee orthosis. Like the previous embodiment, the interface layer 32 surrounds at least a portion of the base frame element 31 and comprises a hinge member 33. The interface layer 32 may also feature the extended portions 40, which extend laterally beyond the periphery of base frame element 31 to provide an especially compliant and soft edge, advantageously minimizing pressure points, enhancing comfort, and providing cushioning and support in key locations.

In an embodiment, the extended portions 40 may be configured to provide a cover for the straps which extend under or through the extended portions 40 and attach to the base frame element 31. In this way, the extended portions 40 prevent interference with and/or damage to the operation of the straps, such as objects catching in the strap attachment mechanism, enhancing safety, durability, aesthetics, and comfort. The extended portions 40 may be configured to extend under for example straps, attachment systems, or tightening systems, thereby cushioning or shielding a user's skin from contact with the article extending over the extended portion 40.

Figure 8:
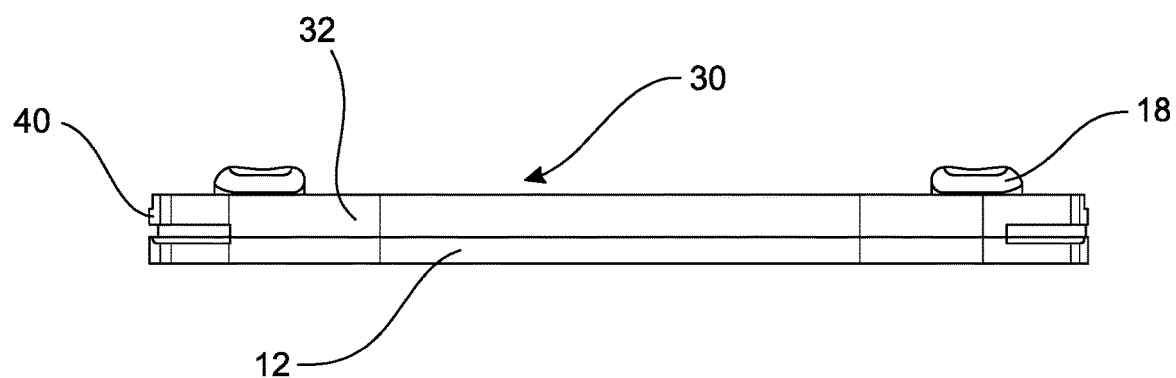
FIG. 8 is an elevational view of the alternative embodiment of FIG. 7 connected to a liner.

FIG. 8 is an elevational view of the overmolded frame element 30 of FIG. 7, and an attached liner 12. The liner 12 is arranged to be substantially coextensive with frame element 30 when in a planar configuration, and owing to its flexible properties, is coextensive with the frame element 30 when in a curved configuration corresponding to a wearer's leg.

Figure 9:
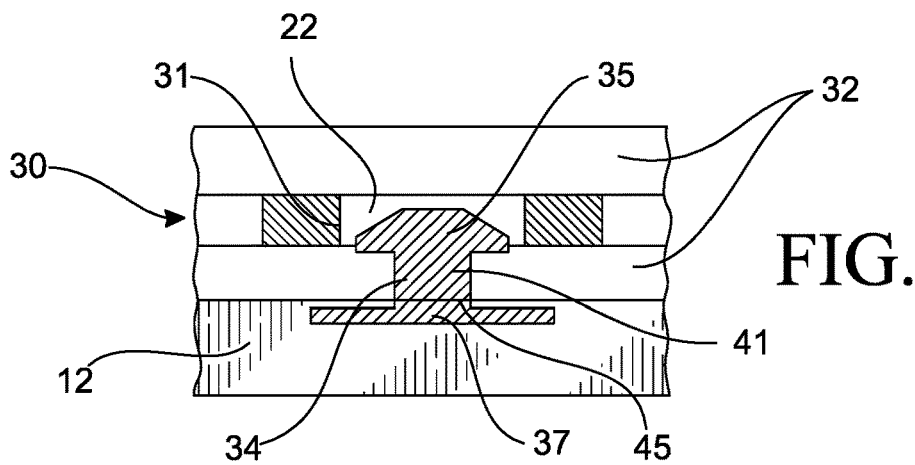
FIG. 9 is an elevational view of the at least one fastener attaching through the at least one aperture provided in the interface layer on the base frame element.

FIG. 9 is an elevational view of the liner 12 removably attaching to the overmolded frame element 30 through the apertures 22, 45. The fastener 34 is configured to non-removably secure to the liner 12 and to removably secure to the overmolded frame element 30 through the interface layer 32 and the base frame element 31, specifically through the apertures 22, 45. In a representative embodiment, the fastener 34 may have a domed head portion 35, which advantageously allows for relatively easy introduction of fastener 34 into the aperture 22 (such as by aligning the fastener 34 with the apertures 22, 45 and then pressing from the liner 12 into the apertures 22, 45), and prevents unintentional removal, but is removable (such as by pulling on the liner 12) by hand.

The fasteners 34 may not extend entirely through the base frame element 31 but may be received by and/or in the apertures 22, 45. The apertures 45 may define a clearance corresponding to the fasteners 34.

The fastening mechanism shown in FIG. 9 improves upon liners that attach via hook and loop by providing a more precise, strong, robust, and easy-to-use attachment process. Because the fasteners 34 and apertures 22, 45 provide a single possible arrangement of the liner 12 relative to the overmolded frame element 30, the liner is attached more precisely than hook and loop, which provides a range of possible attachment configurations, many of which configurations are not desirable or effective. A user mounting the liner 12 with hook and loop fasteners may be obliged to make several attempts at properly mounting the liner before a satisfactory connection is made. By contrast, a user mounting the liner 12 with the mechanism as provided in the disclosure needs to make only one attempt to precisely mount the liner 12 in the ideal configuration.

The connection between the fasteners 34 and apertures 22, 45 is also stronger and more robust than hook and loop fasteners can achieve. The fasteners 34 may be configured with a domed shape head portion 35 and narrow shaft portion 41 to achieve a strong connection within the interface layer 32. Due to the overhanging peripheral edge of head portion 35 within the interface layer 32, the fastener 34 is effectively held in place within the interface layer 32. Similarly, base portion 37 may have a wide lip to non-removably secure the fastener 34 within the liner 12.

The head portion 35 may have a diameter greater than the apertures 22, 45. Accordingly the portion of the interface layer 21 surrounding the aperture 22 stretches to receive the head portion 35 when the fastener 34 is pressed into the aperture 22. After the head portion 35 is inserted into an aperture 22, the portion of the interface layer 21 surrounding the aperture 22 recovers or returns to its original configuration, pressing against the shaft portion 41.

The connection between the fasteners 34 and apertures 22, 45 is easier to use than hook and loop fasteners, which may be difficult and/or cumbersome to properly align, especially as unintended movements cause the hook and loop fasteners to become disoriented or uncoupled during the course of use. Frequent readjustments of the liners that attach via hook and loop fasteners can be especially difficult for elderly persons or people recovering from injury.

With a liner supported on a frame element according to the disclosure, a user simply presses the fastener 34 into the apertures 22, 45, and the liner 12 is reliably secured in place. A "snap" sound or sensation to alert a user of proper introduction of fastener 34 into apertures 22, 45 may further aid in ease and convenience of use.

In an alternative embodiment, base frame element 31 does not comprise apertures 22 corresponding to or providing a clearance for fasteners 34, and fasteners 34 secure only at apertures 45.

Figure 10:
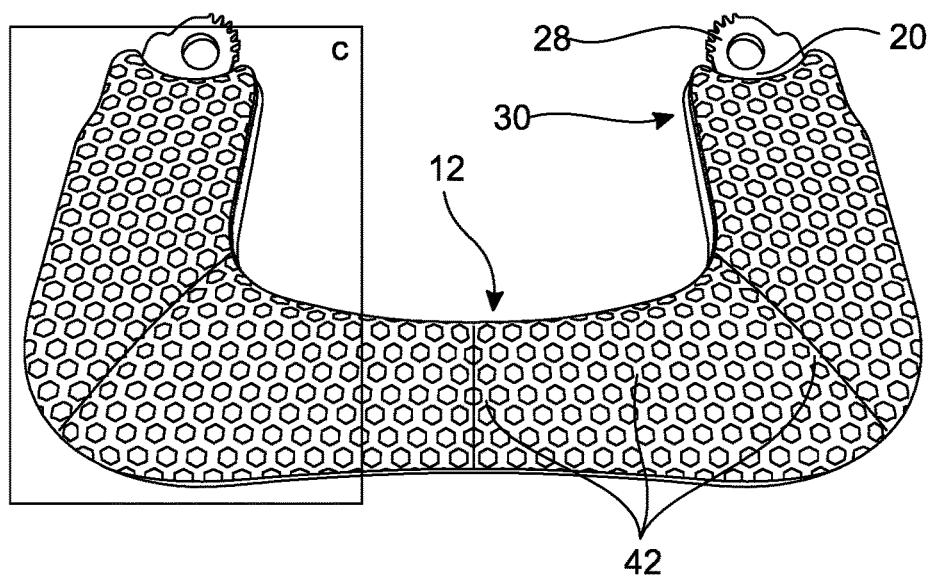
FIG. 10 is a plan view of the inner or user-facing side of the liner attached to the interface layer frame element.

FIG. 10 shows a plan view of the liner 12 attached to the overmolded frame element 30. An inner or user-facing side of the liner 12 is shown. The liner 12 may comprise pinched portions or recessed channels forming the fold lines 42, advantageously allowing the liner 12 to conform to the configuration of the overmolded frame element 30 as determined by a clinician or a user, whether substantially planar, curved, or otherwise. The fold lines 42 also advantageously provide channels whereat the liner 12 may not be in direct contact with a user's skin, facilitating air flow and ventilation of a user's skin. The fold lines 42 may enhance comfort by allowing transfer of heat and moisture.

The fold lines 42 may extend in a substantially symmetrical direction. The direction may be one that will allow the liner 12 to best adapt to a change in shape of the frame element 30. In an exemplary embodiment, the frame element 30 is configured to be malleable to accommodate a user's specific dimensions. The frame element 30 may be bent by a user or practitioner to be more or less curved depending on the size of a user's leg. The fold lines 42 extend in a direction perpendicular to the direction of curvature to allow the liner 12 to bend and curve as the frame element 30 is shaped. The liner 12 advantageously can be adaptable and suitable for frame elements in many configurations.

The liner 12 may comprise distinct layers of material, including at least one core layer comprising compliant material. The at least one core layer of compliant material may be any material providing compressibility, in an exemplary embodiment closed-cell foam. The core layer of compliant material may be bound by one or more outer layers of any material providing desired grip and compliant properties, such as polymeric films, textiles, synthetic fabrics, and other suitable materials. In an exemplary embodiment, compliant material is bounded by doeskin for user comfort and aesthetic appeal. In another exemplary embodiment, compliant material is bounded by cordura material for desired grip and durability properties. In an embodiment, the outer layers are integrally and/or non-removably affixed to the core layer.

An outer layer of material on an inner or user-facing side of the liner 12 may comprise a different material than an outer layer of material on an opposed outer side of the liner 12. The outer layer of material on both the inner or user-facing side and the outer side of the liner 12 may be the same material. The outer layers may be connected to each other at a peripheral edge of the liner 12 and may define thereat a pinched or compressed portion 46 extending slightly laterally outwardly from the peripheral edge.

The inner or user-facing side of the liner 12 may comprise a greater quantity of cushioning and/or compressible material to enhance comfort as the liner abuts a user's anatomy, defining a bulging or rounded profile.

Figure 11:
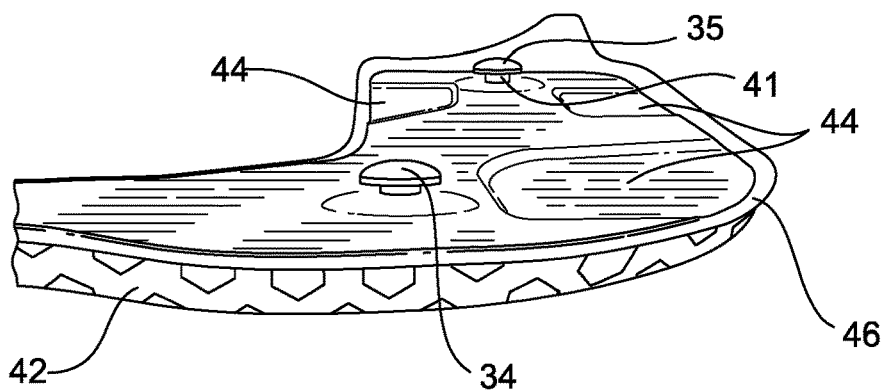
FIG. 11 is a detail profile view of the outer side of the portion of the liner in box c of FIG. 10.

Turning now to FIG. 11, a perspective view of the portion of an outer side of the liner 12 contained in box c in FIG. 10 is shown. An outer side of the liner 12, while generally planar, may comprise recessed portions 44 arranged to correspond to frame attachments such as strap 16, similar to recessed portions 29 of the interface layer 21. The recessed portions 44 advantageously allow for a minimized profile and reduced bulk as frame attachments such as the straps 16 are accommodated within the recessed portions 44 and do not add extra bulk.

The liner 12 may be arranged to be coextensive only with an inner or user-facing surface of the interface layer 32. The liner 12 may also extend laterally outwardly beyond the interface layer 32 as needed, owing to the advantageous use of the fasteners 34 and fold lines 42 which function to support the liner 12 on the overmolded frame element 30 while adapting to any changes in shape of the frame element 31.

The liner and corresponding frame element improve upon and solve problems of existing frame elements and liners by providing a fastening system to attach a liner to a frame element and improve precision of attachment, strength of attachment, durability, and ease of use, while also providing comfort, durability, and compatibility with frame element attachments.

It is understood that while representative embodiments of the disclosure are a removable liner for a frame element in a knee orthosis, the liner for a frame element can be adjusted and implemented in not only a variety of prosthetic and orthopedic devices, but also in any devices where a liner must be attached to a frame element. It is understood by those skilled in the art that the disclosure extends beyond the specifically disclosed representative embodiments to other alternative embodiments and/or uses of the embodiments, and obvious modifications and equivalents thereof. It is intended that the scope of the present disclosure should not be limited by the particular disclosed embodiments described above.

It is to be understood that not necessarily all objects or advantages may be achieved in accordance with any particular embodiment of the disclosure. For example, those skilled in the art will recognize that the liner for a corresponding frame element may be embodied or carried out in a manner that achieves or optimizes one advantage or group of advantages as taught without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a liner for a corresponding frame element.

The invention claimed is:

1. An orthopedic device having a frame element, comprising:
 a liner having at least one core layer of a compliant and closed-cell foam material;
 a base frame element belonging to the frame element and being semi-rigid or rigid;
 at least one fastener connecting the liner to the base frame element, the at least one fastener corresponding to at least one aperture defined by the base frame element, the at least one fastener being configured and dimensioned to removably secure to the base frame element by at the at least one aperture, the at least one fastener being compression molded into the liner and non-removably secured to the liner;
 wherein the liner is configured to flexibly adapt to a shape of the frame element, the liner being substantially more flexible than the base frame element;
 wherein the at least one fastener is arranged to create a "snap" noise or sensation when the at least one fastener is introduced into the at least one aperture;
 the frame element formed from a malleable material;
 wherein the liner defines recessed channels forming fold lines arranged to adapt the liner to conform to the shape of the frame element, the fold lines are arranged in at least one direction perpendicular to a curvature of a portion of the frame element and in at least one direction perpendicular to a length of a portion of the frame element;
 wherein an outer side of the liner being generally planar, and forming at least one recessed portion relative to a plane of the outer side of the liner, the outer side of the liner being located opposite an inner or user-facing side of the liner;
 wherein the at least one fastener comprises a base portion embedded within the liner forming a wide lip configuration being wider than a head portion, a shaft portion extending from the base portion outwardly from the outer side of the liner, the shaft portion culminating in the head portion having an overhanging peripheral edge; an interface layer secured about the base frame element, the interface layer consisting of a thermoplastic elastomer, the interface layer being molded to yield to a shape of the frame element, the interface layer secured to the base frame element without requiring fasteners or adhesive; a surface of the interface layer defines at least one aperture corresponding to the at least one aperture defined by the base frame element, the at least one aperture of the interface layer being configured for the at least one fastener to pass therethrough; wherein the interface layer encases a segment of the base frame element by extending over opposed surfaces thereof between first and second peripheral edges defined by the base frame element; and wherein the at least one aperture extends through a first side of the interface layer, through the entirety of the base frame element, and into but short of the entire thickness of a second side of the interface layer.

2. The orthopedic device of claim 1, wherein the interface layer is formed about a periphery of the base frame element and defines a peripheral edge portion extending beyond the periphery of the base frame element.

3. The orthopedic device of claim 2, wherein the interface layer encases a segment of the base frame element by extending over opposed surfaces thereof between first and second peripheral edges of the base frame element.

4. The orthopedic device of claim 1, wherein when the liner is removably attached to the base frame element by the at least one fastener and the at least one aperture, the liner and the base frame element are arranged substantially flush against each other.

5. The orthopedic device of claim 1, wherein the interface layer defines a recessed portion extending into a thickness of the interface layer short of a surface of the base frame element, wherein a layer of the interface layer covers the base frame element in the recessed portion; wherein the recessed portion immediately abuts the at least one aperture.

6. The orthopedic device of claim 1, wherein the interface layer has a shape closely approximating a shape of the base frame element located between first and second peripheral edges of the base frame element.

7. The orthopedic device of claim 1, wherein the head portion of the at least one fastener has a diameter greater than the at least one aperture.

8. The orthopedic device of claim 3, wherein the interface layer and the base frame element are a single overmolded part.

* * * * *